United States Patent
Darby, II et al.

(10) Patent No.: US 9,387,108 B2
(45) Date of Patent: *Jul. 12, 2016

(54) NIGHT SPLINT WITH DIGITAL DORSIFLEXION

(75) Inventors: H. Darrel Darby, II, Huntington, WV (US); Wu Zhang, Proctorville, OH (US)

(73) Assignee: DARCO INTERNATIONAL, INC., Hunington, WV (US)

(*) Notice: Subject to any disclaimer, the term of this patent is extended or adjusted under 35 U.S.C. 154(b) by 156 days.

This patent is subject to a terminal disclaimer.

(21) Appl. No.: 13/555,482

(22) Filed: Jul. 23, 2012

(65) Prior Publication Data
US 2012/0283612 A1  Nov. 8, 2012

Related U.S. Application Data

(63) Continuation of application No. 12/105,486, filed on Apr. 18, 2008, now Pat. No. 8,226,589.

(51) Int. Cl.
*A61F 5/01* (2006.01)

(52) U.S. Cl.
CPC .............. *A61F 5/0111* (2013.01); *A61F 5/019* (2013.01)

(58) Field of Classification Search
USPC ................... 602/5, 23, 27, 28, 29, 60–62, 65; 128/846, 869, 882, 893; 482/80; 2/60–61, 239, 242
See application file for complete search history.

(56) References Cited

U.S. PATENT DOCUMENTS

| | | | | |
|---|---|---|---|---|
| 4,869,499 A * | 9/1989 | Schiraldo | ........................ | 482/79 |
| 5,010,878 A * | 4/1991 | Kline et al. | ..................... | 601/27 |
| 5,039,093 A * | 8/1991 | Collier | ........................... | 601/27 |
| 5,257,969 A | 11/1993 | Mance | | |
| 5,609,568 A | 3/1997 | Andrews | | |
| 5,702,354 A * | 12/1997 | DeSpain et al. | ................. | 601/27 |
| 5,776,090 A | 7/1998 | Bergmann et al. | | |
| 5,799,569 A | 9/1998 | Moreth | | |
| 5,897,520 A | 4/1999 | Gerig | | |
| 5,928,173 A * | 7/1999 | Unruh | ............................ | 602/30 |
| 6,010,468 A | 1/2000 | Grove et al. | | |
| 6,530,893 B1 * | 3/2003 | Castelli | ........................... | 602/32 |
| 7,179,206 B2 * | 2/2007 | Backes et al. | ................... | 482/80 |
| 7,354,413 B2 | 4/2008 | Fisher | | |
| 7,727,174 B2 * | 6/2010 | Chang et al. | .................... | 602/28 |
| 7,806,844 B2 * | 10/2010 | Outred et al. | ................... | 602/28 |
| 7,828,758 B2 | 11/2010 | Clements et al. | | |
| 8,226,589 B2 * | 7/2012 | Darby, II | ............... | A61F 5/0111 128/882 |
| 8,357,110 B1 * | 1/2013 | Frierson | ........................ | 602/23 |
| 2008/0294083 A1 | 11/2008 | Chang et al. | | |

OTHER PUBLICATIONS

"Phantom Dorsal Night Splint", MedSpec.com, Medical Specialties, Inc., advertisement indicates "patent pending".

* cited by examiner

*Primary Examiner* — Ophelia A Hawthorne (74) *Attorney, Agent, or Firm* — Sughrue Mion, PLLC (57) ABSTRACT

A night splint for a user's foot having a frame member and a toe retainer that is releasably connected to the frame member. The toe retainer is configured to dorsiflex at least one toe of the user to allow for a dynamic stretch of the plantar fascia and to provide a low load stretch of the Achilles tendon, plantar fascia tendon, deep flexor muscles and calf muscles to relieve symptoms of plantar fasciitis.

17 Claims, 14 Drawing Sheets

NIGHT SPLINT WITH DIGITAL DORSIFLEXION

This is a continuation of Application No.: 12/105,486 filed Apr. 18, 2008, now U.S. Pat. No. 8,226,589; the disclosure of which is incorporated herein by reference in its entirety.

BACKGROUND OF THE INVENTION

The present invention generally relates to a splint that can be worn while a user sleeps or rests; the splint holding the foot and ankle at a 90° angle to apply a mild stretch on the calf muscles and the plantar fascia.

The plantar fascia is a fibrous band of tissue that supports the arch of the foot. The plantar fascia extends from the bottom surface of the heel bone to the bottom of the forefoot just behind the toes. If the plantar fascia becomes strained, the arch and heel bone area of the foot can become tender and swollen. This is referred to as plantar fasciitis, a common and painful medical condition of the foot.

Often, plantar fasciitis is caused by inflexibility or tightness of the Achilles tendon, which extends upward from the heel in the back of the lower leg. That is, during physical activity, a person's Achilles tendon can extend beyond a position that normally occurs when one stands, walks, runs, or sits. When the Achilles tendon extends in this way, this places tension and strain on the plantar fascia.

Patients have successfully treated plantar faciitis by wearing a rigid splint at night while sleeping. The splint includes an upper portion and a lower portion, with the lower portion generally extending at an ankle of 90 degrees with respect to the upper portion. By wearing this splint, the patient's foot is maintained in a state of dorsiflexion (i.e., flexion of 90 degrees) and the plantar fascia is prevented from contracting or shortening during the night.

Prior devices for stretching and splinting the leg, ankle and foot attempt to maintain the foot in a 90° angle to stretch the plantar fascia, Achilles tendon and calf muscles by strapping the lower leg and foot to a rigid, dorsal splint formed at a 90° angle. Obtaining dorsiflexion in such a manner rarely achieves the goal of maintaining a position of 90° or less because if the toes are not specifically engaged in the device they tend to plantar flex, which relaxes the plantar fascia and allows the forefoot to drop away from the brace This dropping of the forefoot creates a lever effect on the dorsal splint causing it to pull away from the shin and resulting in a foot/leg angle of substantially greater that 90°. The simultaneous action of the foot and shin pulling away from the rigid splint also creates a pressure point across the neck of the ankle.

Stiffness and/or contracture of the gastrocnemius fascia, Achilles tendon, plantar fascia, posterior tibial tendon, deep flexor muscles and other soft tissues of the foot and ankle are associated with several pathologic conditions. These conditions include but are not limited to: plantar fasciitis, heel spurs, Achilles tendonitis, Achilles tendinosis, metatarsalgia, ankle contracture, painful callosities, and ulcerations. Accordingly, the treatment of these conditions may include the use of exercises, therapy and devices designed to splint and/or stretch the said anatomic structures. One device or class of devices is worn by the patient while at rest, usually at night, and therefore commonly referred to as a "night splint."

To splint and/or stretch the foot while at rest, a variety of devices have been developed. Despite the extensive development of such devices, they continue to exhibit certain disadvantages. The main disadvantage is that no existing device specifically engages and dorsiflexes the toes to provide a specific and sustained stretch to the plantar fascia and to apply tension to the muscles of the foot and leg enough to allow them to easily maintain the 90° angle most practitioners view as optimal for effective treatment of plantar fasciitis.

SUMMARY OF THE INVENTION

In view of the foregoing, aspects of the present invention are provided to allow for a controlled, dynamic stretch of the plantar fascia, by loading the windlass mechanism, to relieve symptoms of plantar fasciitis by providing specific stretching of the plantar fascia and a sustained low load stretch to the Achilles tendon, posterior tibial tendon, deep flexor muscles and calf muscles. In the present invention, by loading the windlass mechanism, these goals are accomplished with a fraction of the force required for the conventional dorsiflexion of the foot provided in prior art devices.

In an illustrative, non-limiting embodiment, a night splint with digital dorsiflexion is provided. The night splint with digital dorsiflexion has a frame member and a toe retainer that is releasably connected to the frame member. The toe retainer is configured to dorsiflex at least one toe of the user.

BRIEF DESCRIPTION OF THE DRAWINGS

Aspects of illustrative, non-limiting embodiments of the present invention will become more apparent by describing in detail embodiments thereof with reference to the attached drawings in which.

DETAILED DESCRIPTION OF THE INVENTION

The following description of illustrative, non-limiting embodiments of the invention discloses specific configurations and components. However, the embodiments are merely examples of the present invention, and thus, the specific features described below are merely used to more easily describe such embodiments and to provide an overall understanding of the present invention. Accordingly, one skilled in the art will readily recognize that the present invention is not limited to the specific embodiments described below. Furthermore, the descriptions of various configurations and components of the present invention that are known to one skilled in the art are omitted for the sake of clarity and brevity.

Figure 1:
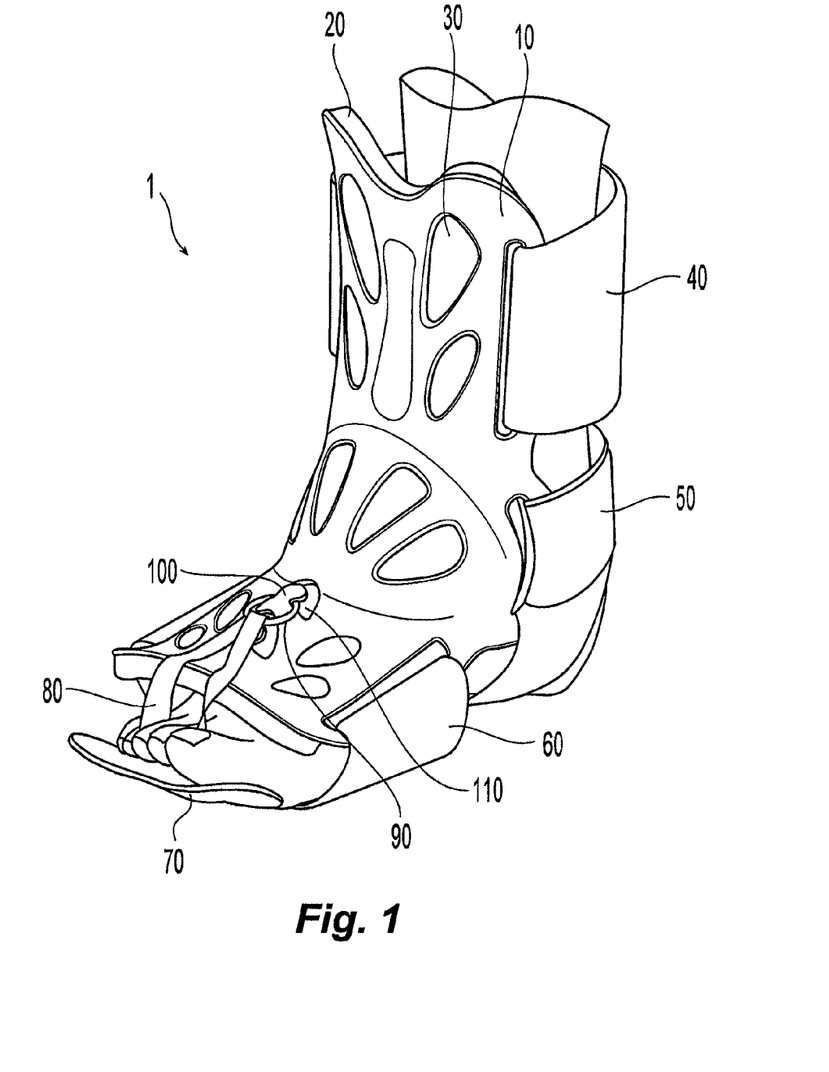
FIG. 1 shows a perspective view of a night splint with digital dorsiflexion.
Figure 2:
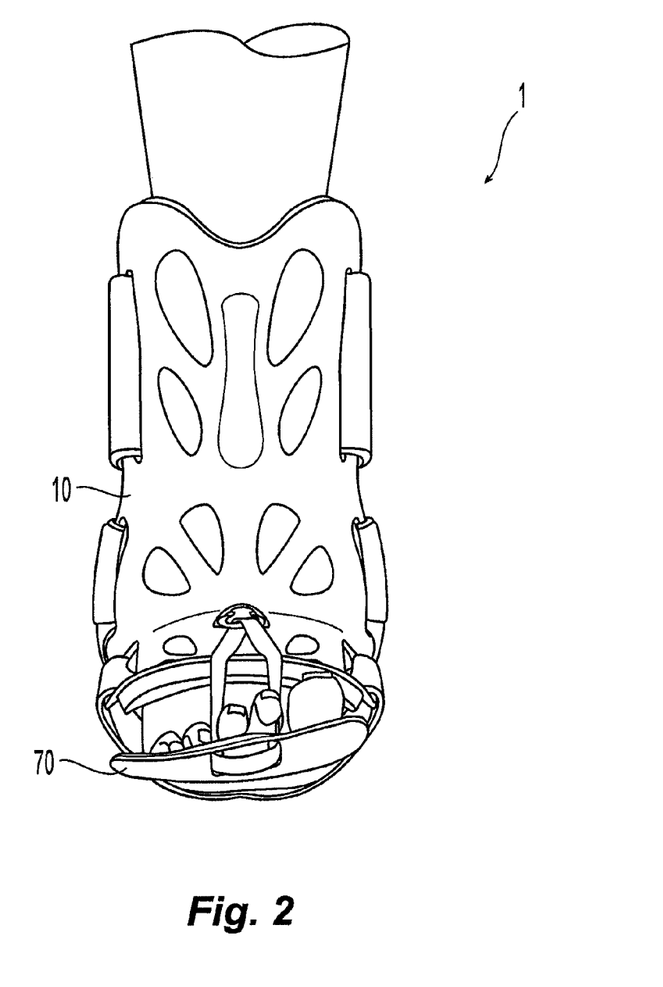
FIG. 2 shows a front view of the night splint with digital dorsiflexion.

FIGS. 1 and 2 show a non-limiting embodiment of the night splint with digital dorsiflexion 1 that provides an easily adjusted plantar fascia stretch, by loading the windlass mechanism, and a sustained low load stretch to the Achilles tendon, plantar fascia tendon, deep flexor muscles and calf muscles to help relieve symptoms of plantar fasciitis.

Windlass mechanics, as mentioned above, is an engineering concept that has been used for thousands of years to help move heavy loads. In relation to the foot, windlass mechanics are important to correct foot function. The windlass mechanism is the coordinated action of the layers of the muscle, tendon, ligament and bony architecture, to maintain arch height and foot rigidity. Without correct windlass function, the foot will not act as an efficient lever, and an effective push off power cannot be achieved. A delay or absence of the onset of the windlass mechanism may play an important role in the incidence of some injuries.

When the hallux or big toe moves upwards or dorsiflexes, the plantar fascia is drawn tightly around the big toe joint, developing tension. This tension within the plantar fascia packs all the joints of the foot tightly together and converts the foot to a rigid structure in preparation for the forward thrust of propulsion. This increased foot rigidity is reflected by the increase in arch height as the forefoot is drawn down closer to the rear of the foot.

The dorsiflex stretch or upward pull of the toes, in the present invention, can be obtained and maintained easily and with little force when compared to the force required for the conventional dorsiflexion stretch of the entire foot itself in conventional night splint devices. Furthermore, since the manipulation of the windlass mechanism naturally moves the foot and ankle more closely to a 90° angle, the device is less likely to pull away from or slide from the user's foot and leg, such that user comfort and product efficacy is greatly increased.

As shown in FIGS. 1 and 2, the night splint with digital dorsiflexion 1 has a substantially L-shaped frame member or splint 10. The splint 10 is configured to generally conform to the front surface of the lower portion of the user's leg and the upper surface of the user's foot. The splint 10 can be formed of any rigid or semi-rigid material such as metal or plastic. In a non-limiting embodiment, the splint 10 is formed of an injection molded plastic such as polypropylene.

The inner surface of the splint 10 is provided with a liner 20 that contacts the respective foot and leg of the user. The liner 20 can be made of any soft, conforming material. The splint 10 is also provided with ventilation holes 30. As shown, the liner 20 covers the ventilation holes 30. The ventilation holes 30 can vary in size, shape and location, and do not necessarily need to be covered by the liner 20.

Various straps are provided to attach the night splint with digital dorsiflexion 1 to the user. In the non-limiting embodiment of FIG. 1, an ankle strap 40, a heel strap 50 and a foot strap 60 are shown. Each strap can be made of any type of material that contours and fits the foot and leg of a user. Preferably, the straps are formed of a breathable fabric for user comfort. The size, position and thickness of each strap can vary, as long as at least two straps are provided, i.e., one strap for the lower leg and one strap for the foot to retain the night splint with digital dorsiflexion 1 on the user. Furthermore, the straps can be made adjustable via hook-and-loop fasteners, snaps, etc.

Figure 3:
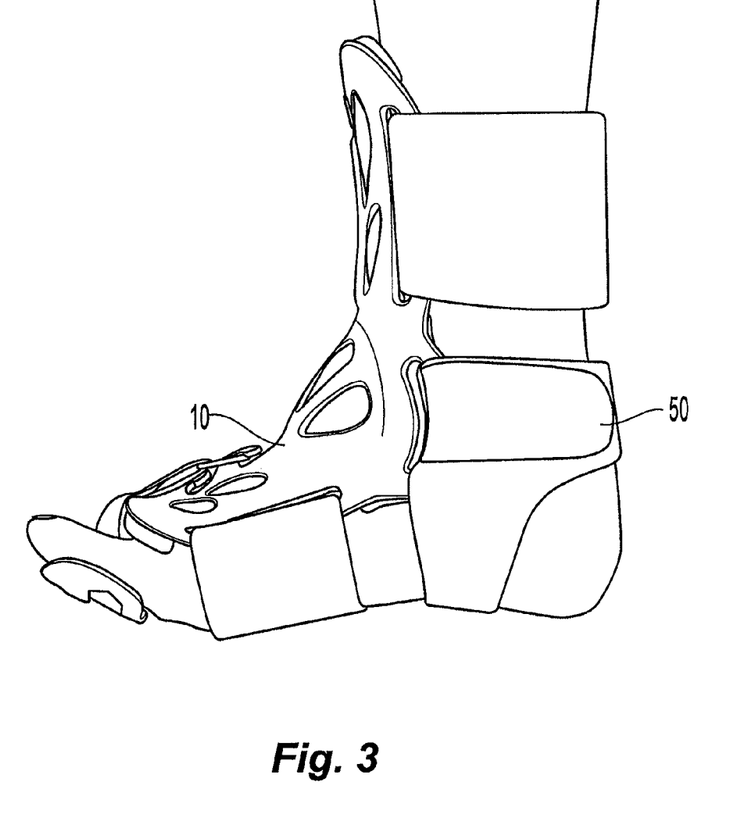
FIG. 3 shows a side view of the night splint with digital dorsiflexion.

The night splint with digital dorsiflexion 1 is also provided with a toe plate 70. As shown in FIGS. 1-3, the toes of the user rest on the toe plate 70. The toe plate 70 connects with the splint 10 via an adjustable flexure strap 80 to flex and retain the toes at a desired stretch. In the non-limiting embodiment of FIG. 1, the flexure strap 80 is permanently connected to the toe plate 70. Of course, the flexure strap 80 can be made detachable from the toe plate 70 using any suitable connection.

At an opposite end thereof, the flexure strap 80 is attached to a connector 90 which in turn attaches to a stretch adjustment portion 100 of the splint 10 for easy adjustment of the dorsiflexion of the toes. As shown, there are two slots 110 at which the connector 90 can easily be attached to the stretch adjustment portion 100 to control the degree of loading of the windlass mechanism or dorsiflexion stretch of the toes. Although in this non-limiting embodiment, the stretch adjustment portion 100 is provided near the toe region of the splint 10, the stretch adjustment portion 100 can be provided at any portion along the splint 10 so long as a proper stretch is provided. Furthermore, although two slots 110 are shown, the number of slots 110 can vary so long as at least one slot or connection point is provided. In this regard, patients begin with a gradual stretch and progress as the condition improves. In an alternate embodiment, the flexure strap 80 itself can have an adjustable length to provide the various degrees of desired dorsiflexion of the toes.

The flexure strap 80 is formed of a non-elastic material, such as a nylon web, to ensure that the desired degree of dorsiflexion of the toes is maintained. Any other suitable non-elastic or rigid material can be used. Of course, an elastic material may be used to form the flexure strap 80. Depending on the degree of elasticity, however, the desired degree of toe dorsiflexion may be difficult to maintain.

Furthermore, in this non-limiting embodiment, the connector 90 comprises a single ring portion that attaches to both the flexure strap 80 and to a respective slot 110. In a non-limiting embodiment, the connector 90 is formed of an elastic material, such as rubber, to allow flexure of a user's foot and toes during stretching or moving while sleeping or resting. In other words, the flexibility allows slight mobility of the foot and toes, yet urges the toes back to the desired angle of dorsiflexion when the foot is again relaxed. Of course, the connector 90 can be formed of a non-flexible material. In such an embodiment, however, flexibility would be reduced.

The connector 90 can alternately be formed in any other various shape that can latch on to the slots 110 for connection thereof. Likewise, in other non-limiting embodiments, the slot 110/connector 90 combination can be replaced with snaps, hook-and-loop fasteners, buckles, etc. Furthermore, the flexure strap 80 can be formed to loop through a ring or other attachment mechanism on the splint 10 and attach back to itself.

FIG. 3 shows a side view of the night splint with digital dorsiflexion 1. As clearly shown in this view, the heel strap 50 wraps around the heel, but does not actually cover the heel itself. Since the present invention merely stretches the toes, the possibility of the splint pulling off the foot is reduced, i.e., less force is used. Accordingly, the heel strap 50 is not required to cover the entire heel, which in turn increases user comfort. Of course, various modifications are applicable.

In FIG. 3, it is further shown that the portion of the splint 10, near the toe region, flares upward away from the toes. This allows for free range of motion of the toes during use of the toe plate 70. Of course, the contour and length of the splint 10 are not limited to the non-limiting embodiments depicted in the figures of the present Application.

Figure 4:
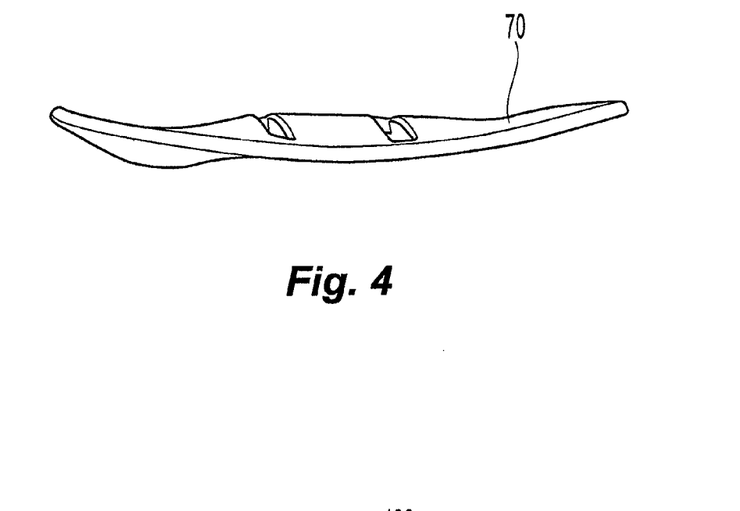
FIG. 4 shows a front view of a toe plate of the night splint with digital dorsiflexion.
Figure 5:
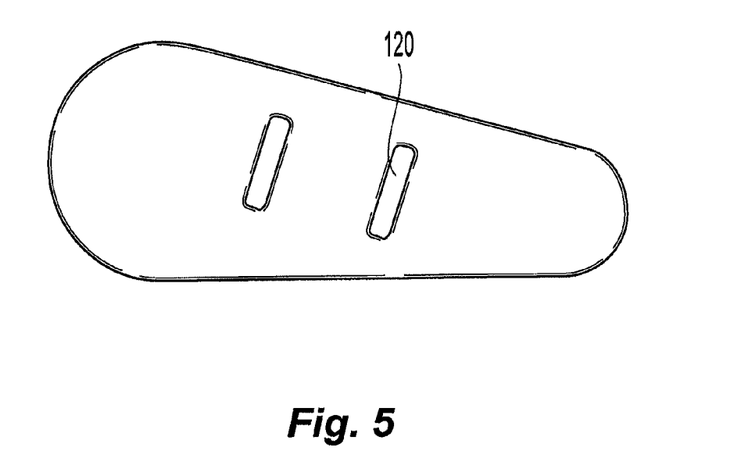
FIG. 5 shows a top view of the toe plate of the night splint with digital dorsiflexion.

FIGS. 4 and 5 depict a non-limiting embodiment of the toe plate 70. The toe plate 70 is contoured and tapered to fit comfortably under the toes and can be formed of a similar material as the splint 10. Slots 120 are clearly visible in these figures. The flexure strap 80, which is formed as a loop, is threaded through the slots 120 of the toe plate 70. The slots 120 are provided in a substantially center portion of the toe plate 70 such that all toes are urged upward when the connector 90 is attached to the stretch adjusting portion 100 of the splint 10. Of course, the toe plate 70 can be formed in any suitable shape and can be made flat. Furthermore, it is not necessary that all toes are dorsiflexed. So long as the toe plate 70 is sized such that at least the hallux or big toe is dorsiflexed, the appropriate stretch of the plantar fascia is achieved. Furthermore, the flexure strap 80 can alternately be formed as a single strip that connects at one end to the toe plate 70 and at the opposite end to the splint 10.

Figure 6:
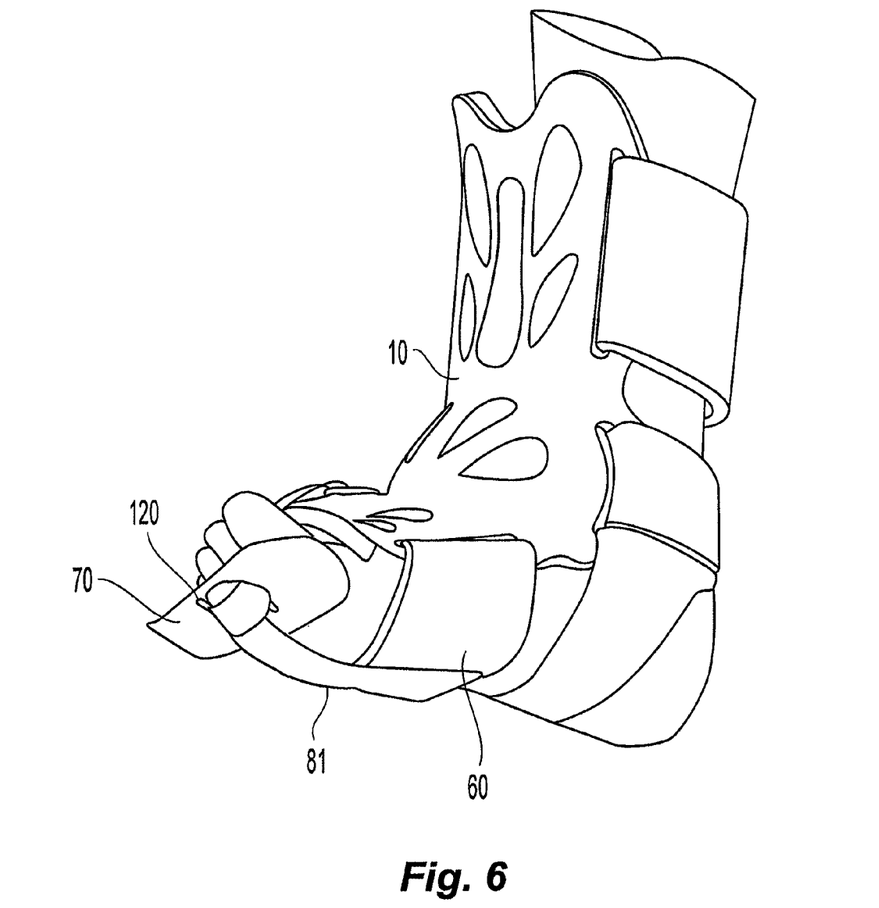
FIG. 6 shows a perspective view of an alternate embodiment of a toe retainer of the night splint with digital dorsiflexion.

FIG. 6 depicts an alternate, non-limiting embodiment where the toe plate 70 is provided with a second flexure strap 81 that is connected at one end to the toe plate 70, via the slots 120, and connected to the foot strap 60 at a second end. The second flexure strap 81 can be permanently attached to the toe plate 70 and the foot strap 60 or removably attached to each element via snaps, hook-and-loop fasteners, buckles, etc. The provision of the second flexure strap 81 aids in securing the position of the toe plate 70.

Figure 7A:
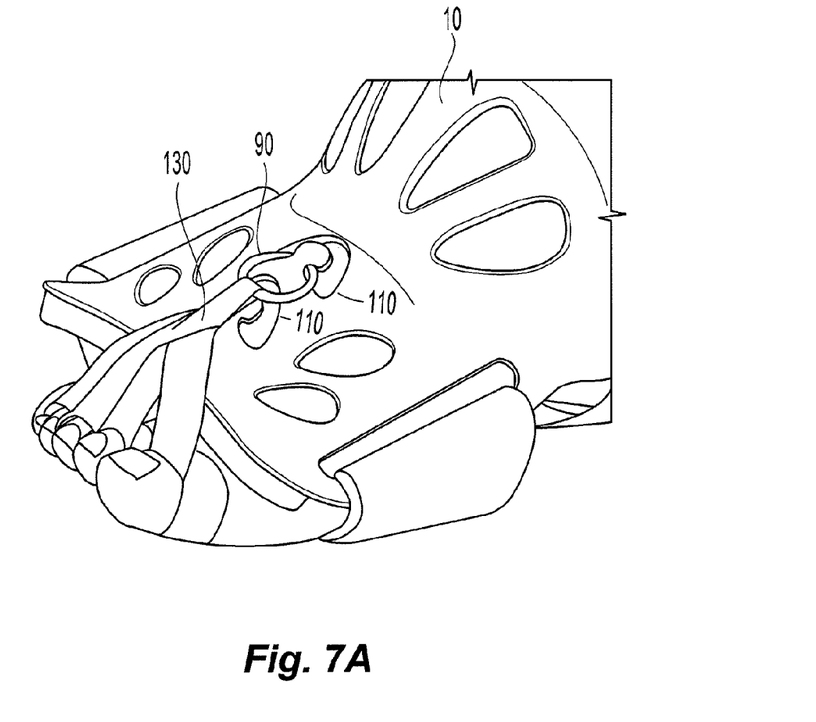
FIG. 7A shows a perspective view of an alternate embodiment of a toe retainer of the night splint with digital dorsiflexion.
Figure 7B:
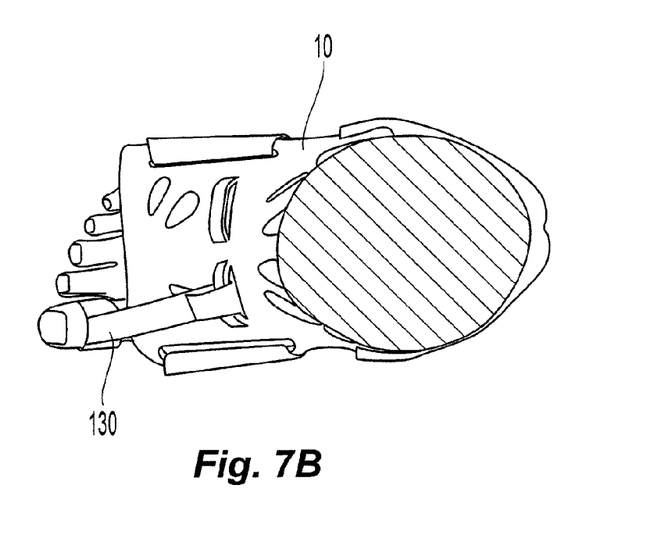
FIG. 7B shows a top view of an alternate embodiment of a toe retainer of the night splint with digital dorsiflexion.

FIG. 7A depicts an alternate, non-limiting embodiment for retaining the toes in a proper stretch of the plantar fascia. As shown, the toes are retained by a divided flexure strap 130 that is connected at one end to the connector 90 and at the opposite end is divided into individual straps that retain the toes in a state of flexure. The divided flexure strap 130 retains the toes in a similar manner as FIG. 1, but without the use of the toe plate 70. The divided flexure strap 130 can alternately be formed to only retain a few toes, but must at least retain the hallux or big toe for proper stretch of the plantar fascia. For example, as shown in FIG. 7B, the flexure strap 130 is formed to retain only the big toe.

Figure 8A:
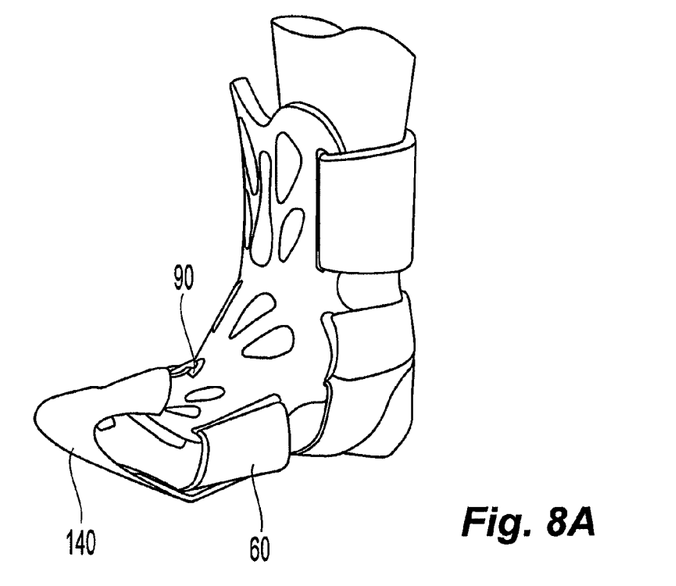
FIGS. 8A, 8B and 8C show perspective views of alternate embodiments of a toe retainer of the night splint with digital dorsiflexion.
Figure 8B:
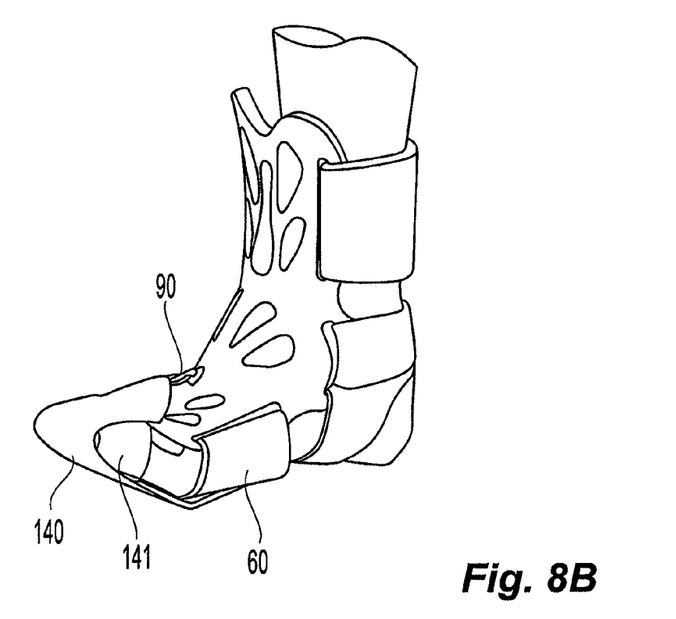
Figure 8C:
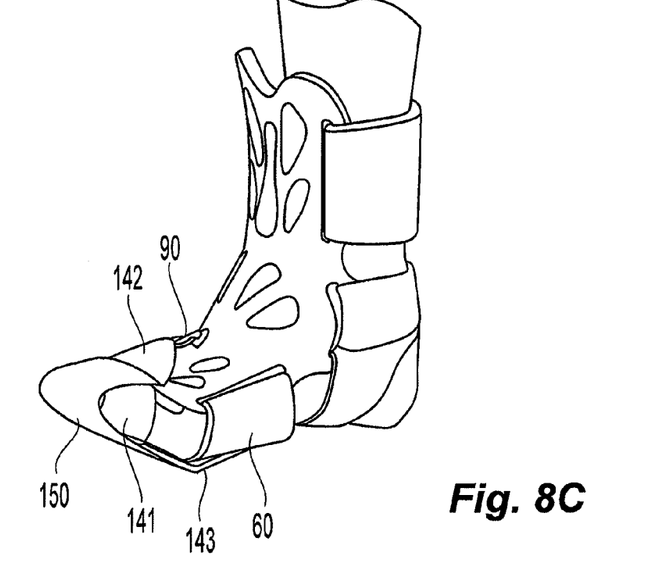

FIGS. 8A, 8B and 8C depict further non-limiting embodiments for retaining the toes in a proper stretch of the plantar fascia without the use of the toe plate 70. As shown in FIG. 8A, the toes are retained by a front cover flexure strap 140 that is connected to the connector 90 at one end, wraps over the front of the toe region and connects to the foot strap 60 at a second end. The front cover flexure strap 140 can be permanently attached to the foot strap 60 or removably attached thereto via snaps, hook-and-loop fasteners, buckles, etc.

FIG. 8B shows the front cover flexure strap 140 of FIG. 8A with the added feature of a side cover flexure strap 141 attached thereto either permanently or in a removable manner. Although not shown, the side cover flexure strap 141 is provided on both outer sides of the front cover flexure strap 140 (i.e., right and left sides of a user's toe region) and aids in preventing the front cover flexure strap 140 from slipping off the toe region.

FIG. 8C shows an alternate embodiment of the front cover flexure strap 140. In particular, a curved shell 150 is provided to cover the toe region. The shell 150 can be formed of any rigid or semi-rigid material such as metal or plastic. The shell 150 connects to the connector 90 via a top cover flexure strap 142 and connects to the foot strap 60 via a bottom cover flexure strap 143. The bottom cover flexure strap 143 can be permanently attached to the foot strap 60 or removably attached thereto via snaps, hook-and-loop fasteners, buckles, etc. As shown, the side cover flexure straps 141 are provided. This embodiment, however, can be formed without the side cover flexure straps 141.

The second flexure strap 81, the divided flexure strap 130, the front cover flexure strap 140, the side cover flexure strap 141, the top cover flexure strap 142 and the bottom cover flexure strap 143 are formed of a non-elastic material, such as a nylon web, to ensure that the desired degree of dorsiflexion of the toes is maintained. Any other suitable non-elastic or rigid material can be used. Of course, an elastic material may be used to form these features. Depending on the degree of elasticity, however, the desired degree of toe dorsiflexion may be difficult to maintain.

Figure 9:
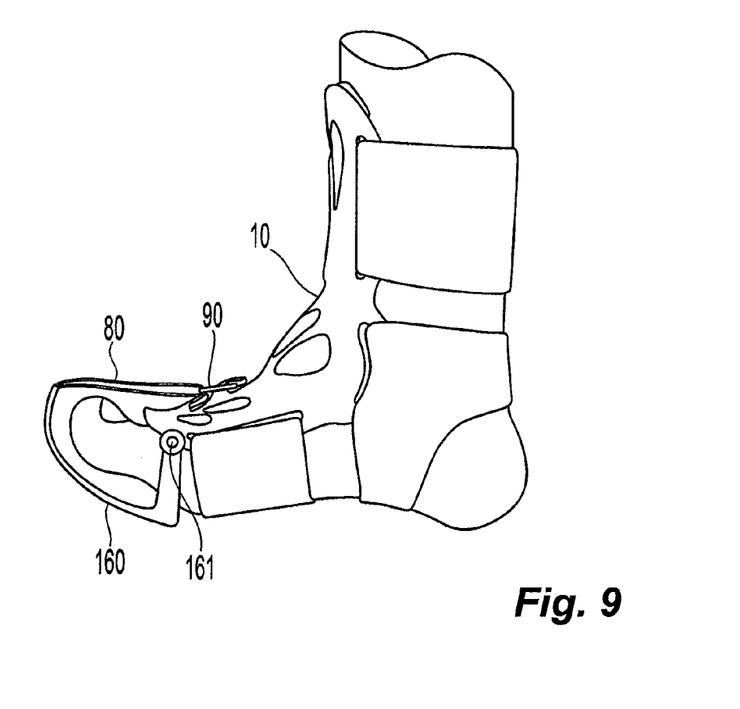
FIG. 9 shows a side view of an alternate embodiment of a toe retainer of the night splint with digital dorsiflexion.

FIG. 9 shows yet another alternate embodiment for retaining the toes in a proper stretch of the plantar fascia. A pivotable front shell 160 is connected to the connector 90 via the flexure strap 80 at one end, curves around and under the toe region and connects to a front side of the splint 10 via the hinge 161 at another end thereof. The front shell 160 can be formed of any rigid or semi-rigid material such as metal or plastic. The hinge 161 allows the front shell 160 to easily rotate in a clockwise or counterclockwise direction to increase or decrease the stretch of the plantar fascia as needed.

Figure 10A:
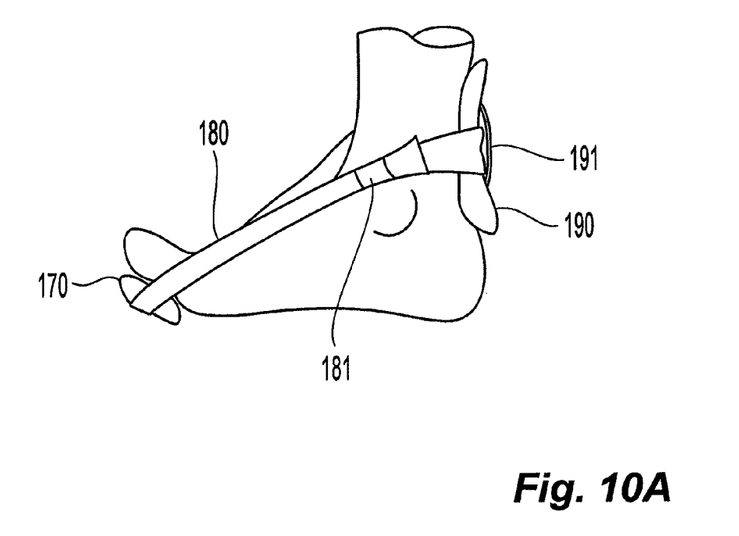
FIG. 10A shows a side view of an alternate embodiment of a toe retainer of the night splint with digital dorsiflexion.

FIGS. 10A to 14B shows various non-limiting embodiments for retaining the toes in a proper stretch of the plantar fascia without the use of the splint 10. As shown in FIG. 10A, a stretch of the plantar fascia is performed by using a toe pad 170 connected to a flexure strap 180. To ensure proper stretch of the plantar fascia, the flexure strap 180 should be formed of a non-stretchable or non-elastic material, such as leather, nylon or cloth. The length of the flexure strap 180 can be increased or decreased, via a buckle 181, to increase or decrease the stretch of the plantar fascia. Of course, any other form of secure attachment means can be used in place of the buckle 181. For support and comfort, the flexure strap 180 is threaded through a loop 191 of an ankle pad 190 at the user's heel/ankle area. The toe pad 170 and the ankle pad 190 can be formed of any type of cushion material, such as foam coated with a fabric. Alternatively, both the toe pad 170 and the ankle pad 190 can be formed of a semi-rigid plastic.

Figure 10B:
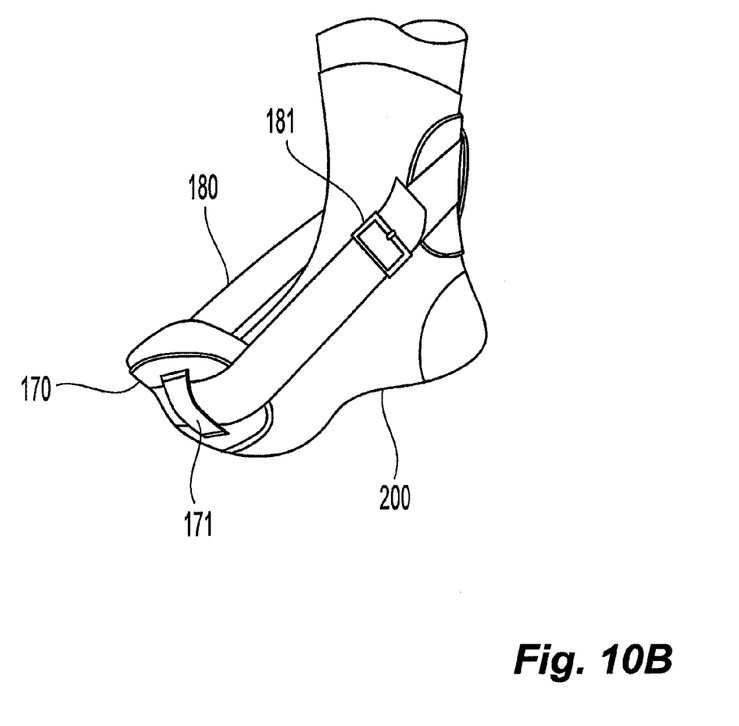
FIG. 10B shows a perspective view of an alternate embodiment of the toe retainer of FIG. 10A.

FIG. 10B shows a perspective view of an alternate embodiment of the toe retainer of FIG. 10A. In particular, a foot sock 200 is used to help retain the toe pad 170 on the toe region of the user. As shown in this view, the flexure strap 180 is connected to the toe pad 170 via the loop 171. The toe pad 170 can alternatively be formed integrally with the foot sock 200.

Figure 10C:
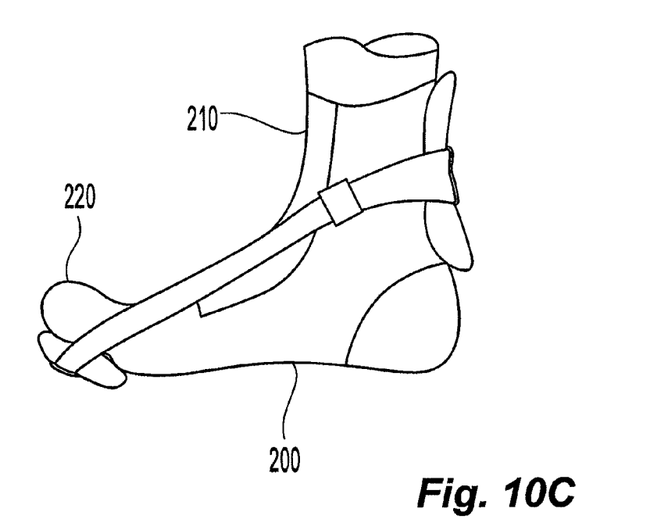
FIG. 10C shows a side view of an alternate embodiment of the toe retainer of FIG. 10B.

FIG. 10C shows a side view of an alternate embodiment of the toe retainer of FIG. 10B. In this embodiment, the foot sock 200 has a semi-rigid plastic shell 210 that is formed to mold to the upper portion of a user's foot and ankle region for added stability.

Figure 11A:
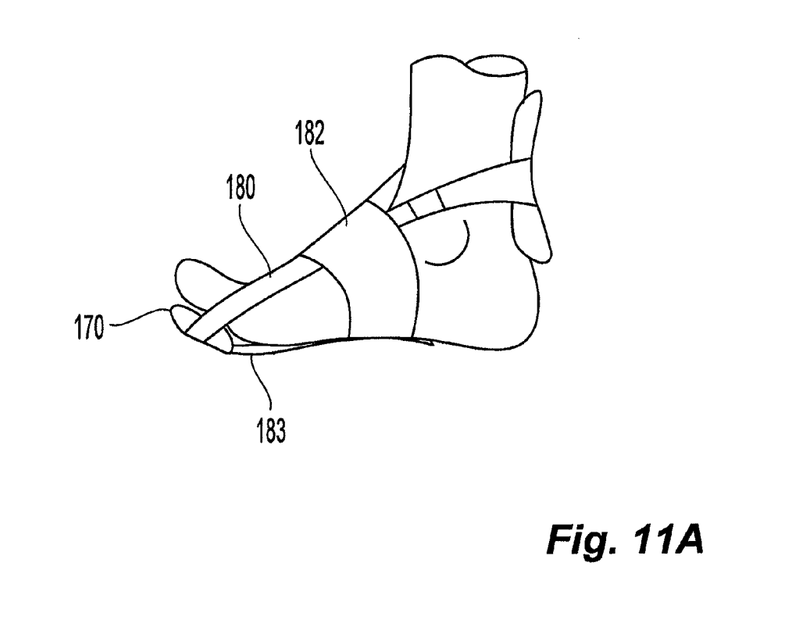
FIG. 11A shows a side view of an alternate embodiment of a toe retainer of the night splint with digital dorsiflexion.

FIG. 11A shows a side view of an alternate embodiment of a toe retainer of the night splint with digital dorsiflexion. In this embodiment, a foot strap 182 is used to help retain the flexure strap 180 in place. The foot strap 182 is shown as wrapping around the foot. Further provided is a second flexure strap 183 that attaches to the toe pad 170 at one end, and to the foot strap 182 at its opposite end, to help prevent the toe pad 170 from slipping off the user's foot. The foot strap 182 can be formed of an elastic material such as spandex and the second flexure strap 183 can be formed of a non-elastic material such as nylon. Furthermore, the second flexure strap 183 can be integrally connected to the toe pad 170, while releasably connected to the foot strap 182, via hook-and-loop fasteners, snaps, etc.

Figure 11B:
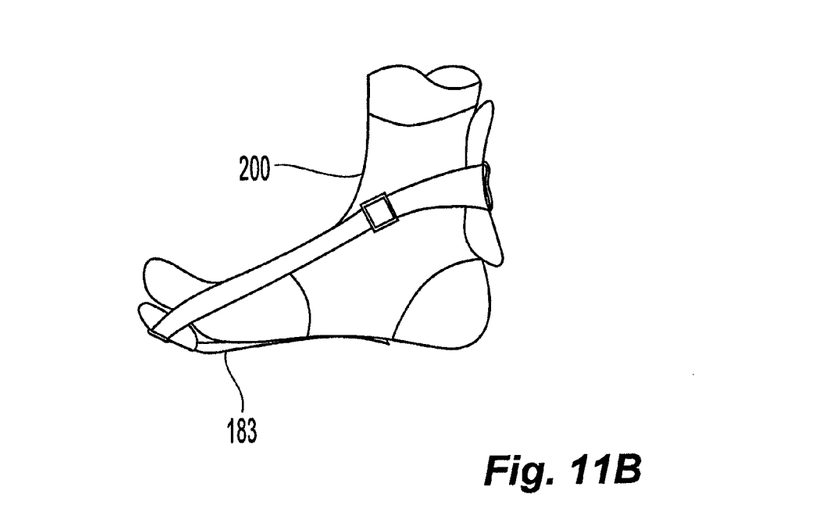
FIGS. 11B and 11C show side views of alternate embodiments of the toe retainer of FIG. 11A.
Figure 11C:
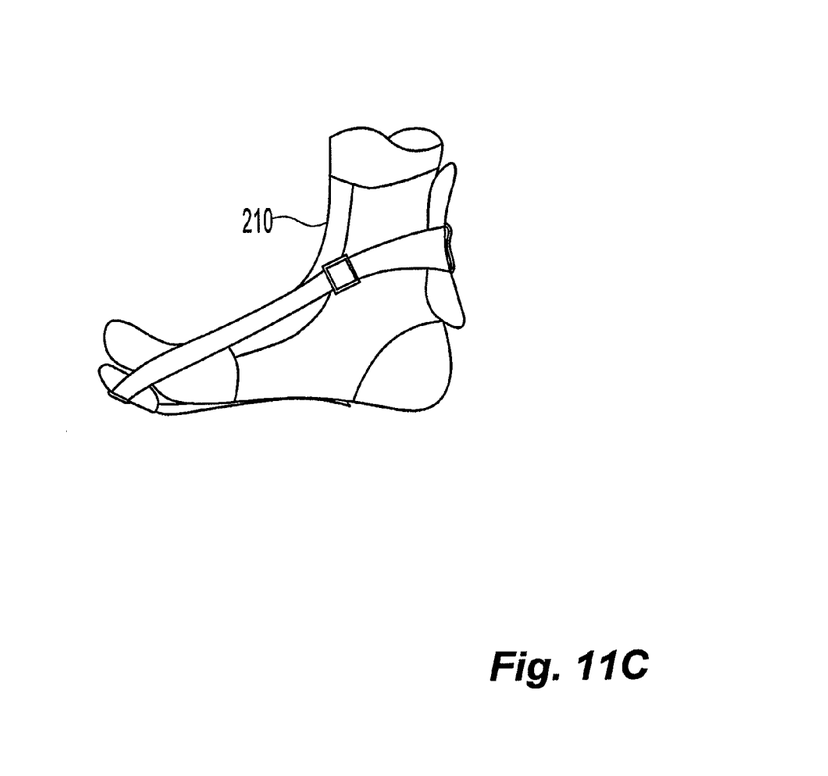

FIGS. 11B and 11C show side views of alternate embodiments of the toe retainer of FIG. 11A. In FIG. 11B, a foot sock 200 is utilized in place of the foot strap 182. Accordingly, the second flexure strap 183 is releasably connected to the foot sock 200. FIG. 11C is similar to the embodiment of FIG. 11B except that the foot sock 200 is provided with the semi-rigid plastic shell 210.

Figure 12A:
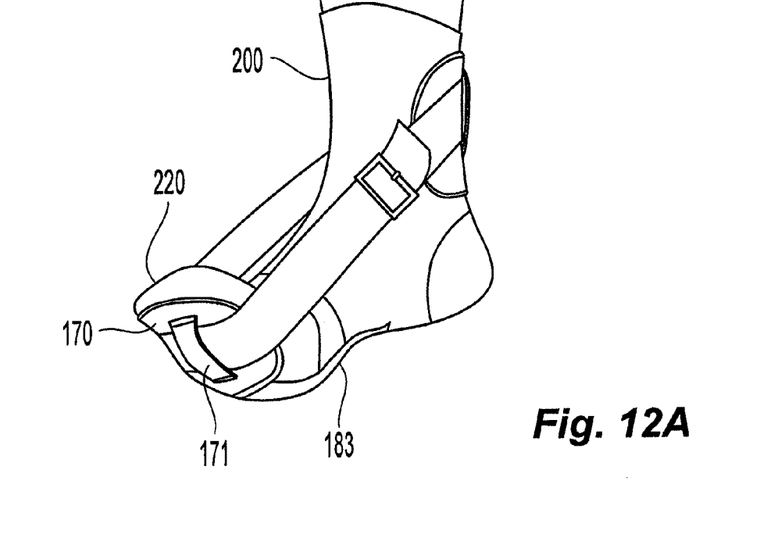
FIG. 12A shows a perspective view of an alternate embodiment of a toe retainer of the night splint with digital dorsiflexion.
Figure 12B:
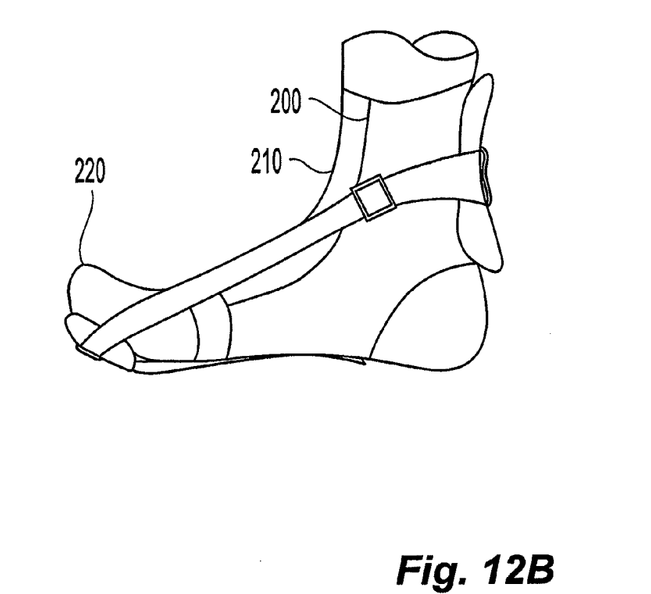
FIG. 12B shows a side view of an alternate embodiment of the toe retainer of FIG. 12A.

FIG. 12A shows a perspective view of an alternate embodiment of a toe retainer of the night splint with digital dorsiflexion. The embodiment of FIG. 12A is similar to the embodiment of FIG. 11B, except that a toe cap sock portion 220 is provided. The toe cap sock portion 220 helps retain the toe pad 170 on the user's toe region as well as aids in protecting the toes. The toe cap sock portion 220 can be reinforced with either a semi-rigid material or a cushioned material. FIG. 12B shows a side view of an alternate embodiment of the toe retainer of FIG. 12A. In particular, the embodiment of FIG. 12B has the added feature of the semi-rigid plastic shell 210 provided on the foot sock 200.

Figure 13A:
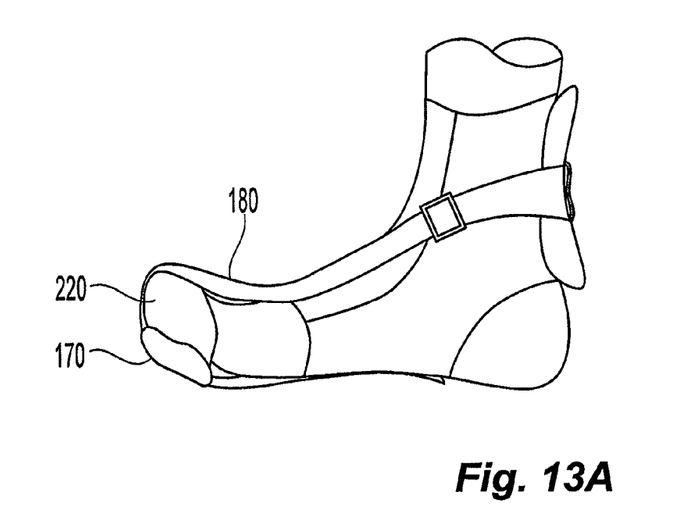
FIGS. 13A and 13B show side views of alternate embodiments of the toe retainer of FIG. 12B.
Figure 13B:
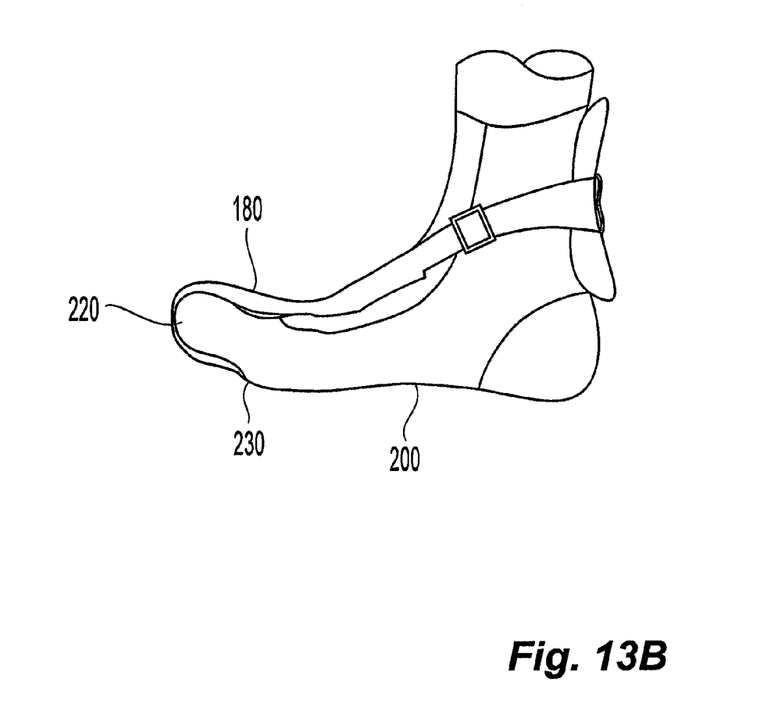

FIGS. 13A and 13B show side views of alternate embodiments of the toe retainer of FIG. 12B. The non-limiting embodiment of FIG. 13A differs from the embodiment of FIG. 12B in that the flexure strap 180 is formed to curve over the top of the toe cap sock portion 220 before connecting to the toe pad 170. In this embodiment, the flexure strap 180 is integrally connected to the toe pad 170. In the embodiment of FIG. 13B, the flexure strap 180 also curves over the top of the toe region, however, the toe pad 170 is not provided. Accordingly, the flexure strap 180 integrally connects to the foot sock 200 underneath the toe region at point 230.

Figure 14A:
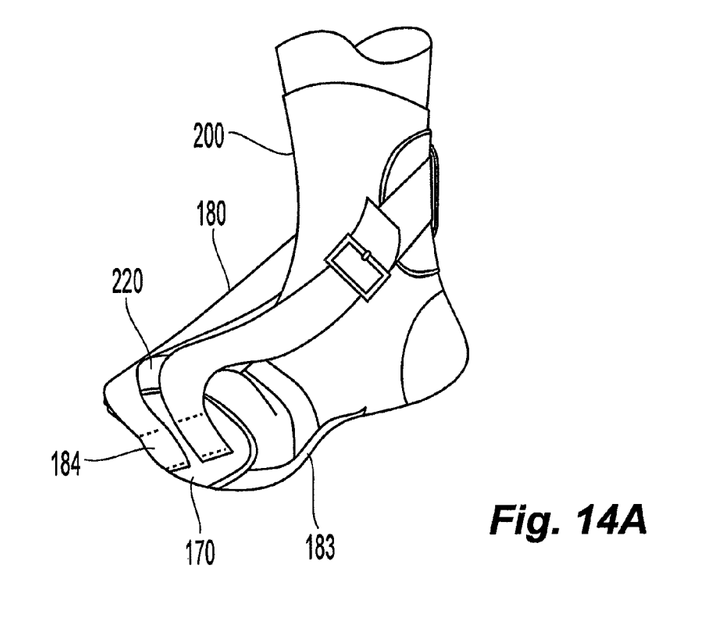
FIGS. 14A and 14B show perspective views of alternate embodiments of FIGS. 10A and 11A.
Figure 14B:
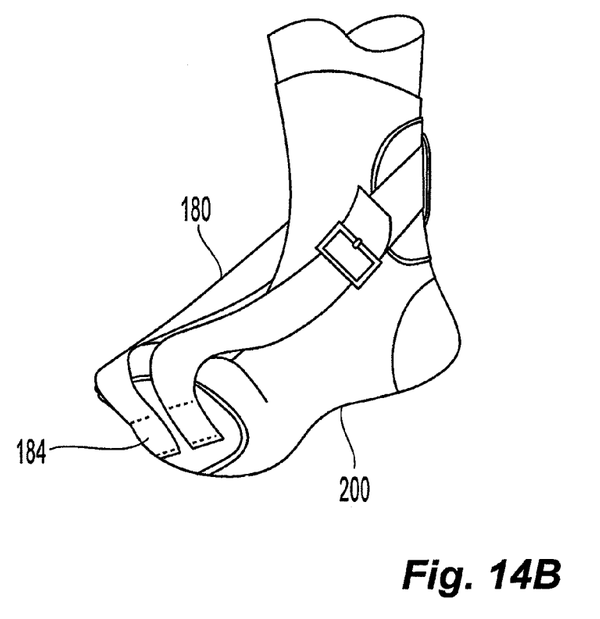

In the non-limiting embodiments of FIGS. 14A and 14B, the flexure strap 180 has two ends 184 that connect to the toe pad 170. The ends 184 of the flexure strap 180 can be integrally formed with the toe pad 170 via stitching, etc.

The previous description of the non-limiting embodiments is provided to enable one skilled in the art to make and use the present invention. Moreover, various modifications to these embodiments will be readily apparent to those skilled in the art, and the generic principles and specific examples defined herein may be applied to other embodiments without the use of inventive faculty. Therefore, the present invention is not intended to be limited to the embodiments described herein, but is to be accorded the widest possible scope as defined by the recitations of the claims and equivalents thereof.

What is claimed is:

1. An apparatus comprising:
a frame member; and
a toe retaining strap configured to dorsiflex only one toe of a user,
wherein the toe retaining strap releasably connects to the frame member at a first end thereof, and is configured to be attached directly to one toe at a second end thereof, the first end and the second end of the toe retaining strap being integrally formed,
wherein the frame member has a leg portion which conforms to a front portion of the user's leg and a foot portion which conforms to a top portion of the user's foot, and the leg portion and the foot portion are connected to each other together form a substantially L-shape,
wherein the toe retaining strap releasably connects to the frame member at the foot portion.

2. The apparatus according to claim 1, wherein the first end of the toe retaining strap releasably connects to the frame member via hook-and-loop fasteners.

3. The apparatus according to claim 2, wherein the first end of the toe retaining strap connects to the frame member at a connection portion comprising a lower portion of the frame member.

4. The apparatus according to claim 3, wherein dorsiflexion of the one toe is varied depending upon where on the connection portion the first end of the toe retaining strap is connected.

5. The apparatus according to claim 1, further comprising: a foot sock having a semi-rigid shell.

6. The apparatus according to claim 5, wherein the second end of the toe retaining strap is configured to connect to the foot sock underneath a toe region.

7. The apparatus according to claim 5, wherein a toe plate is provided at the second end of the toe retaining strap outside the foot sock.

8. The apparatus according to claim 1, wherein the first end of the toe retaining strap is formed of a non-elastic material.

9. The apparatus according to claim 1, wherein the toe retaining strap is adapted to wrap around the foot.

10. An apparatus comprising:
a frame member; and
a toe retaining strap configured to dorsiflex only one toe of a user,
wherein the toe retaining strap releasably connects to the frame member at a first end thereof, and is configured to be attached directly to one toe at a second end thereof, and
wherein the frame member comprises a stretch adjustment portion having at least one connection point and the toe retaining strap releasably connects to the at least one connection point
wherein the frame member has a leg portion which conforms to a front portion of the user's leg and a foot portion which conforms to a top portion of the user's foot, and the leg portion and the foot portion are connected to each other together form a substantially L-shape,
wherein the toe retaining strap releasably connects to the frame member at the foot portion.

11. The apparatus according to claim 10, wherein the first end of the toe retaining strap connects to the stretch adjustment portion via hook-and-loop fasteners.

12. The apparatus according to claim 11, wherein the stretch adjustment portion comprises a lower portion of the frame member that is configured to be attached to a top portion of a foot of the user.

13. The apparatus according to claim 11, wherein dorsiflexion of the one toe is varied depending on which position from at least two positions on the stretch adjustment portion the first end of the toe retaining strap is connected, each of the at least two positions position forming a respective connection point.

14. . The apparatus according to claim 10, wherein the first end of the toe retaining strap is formed of a non-elastic material.

15. An apparatus comprising:
a frame member; and a toe retaining strap configured to dorsiflex at least one toe of a user, wherein the toe retaining strap releasably connects to the frame member at a first end thereof, and is configured to be attached directly to at least one toe at a second end thereof, wherein a toe plate is located at the second end of the toe retaining strap, the toe plate configured to retain the at least one toe at a desired dorsiflexion, wherein the frame member has a leg portion which conforms to a front portion of the user's leg and a foot portion which conforms to a top portion of the user's foot, and the leg portion and the foot portion are connected to each other together form a substantially L-shape, wherein the toe retaining strap releasably connects to the frame member at the foot portion.

16. The apparatus according to claim 15, wherein the one toe is configured to rest on the toe plate such that dorsiflexion of the one toe is performed.

17. The apparatus according to claim 15, wherein the toe retaining strap is configured to dorsiflex the at least one toe, the toe retaining strap being configured to be positioned underneath the toe plate and configured to connect to the frame member.

* * * * *